United States Patent [19]

Worst

[11] Patent Number: 5,180,362
[45] Date of Patent: Jan. 19, 1993

[54] GONIO SETON

[76] Inventor: J. G. F. Worst, Julianalaan 11, 9751 BM, Haren, Netherlands

[21] Appl. No.: 503,690

[22] Filed: Apr. 3, 1990

[51] Int. Cl.$^5$ .............................................. A61M 5/00
[52] U.S. Cl. ...................................... 604/8; 604/164; 604/264; 604/294; 606/108
[58] Field of Search ...................................... 604/8–11, 604/164, 264, 294; 623/4, 5, 6; 606/108, 170, 171; 600/20

[56] References Cited

U.S. PATENT DOCUMENTS

| | | | |
|---|---|---|---|
| 4,030,480 | 6/1977 | Meyer | 600/10 |
| 4,340,037 | 7/1982 | Lewicky | 600/20 X |
| 4,787,885 | 11/1988 | Binder | 604/8 |
| 4,865,601 | 9/1989 | Caldwell et al. | 623/5 |
| 4,915,684 | 4/1990 | Mackeen et al. | 604/8 |
| 4,936,825 | 7/1990 | Ungerleider | 604/8 |
| 4,968,296 | 11/1990 | Ritch et al. | 604/294 X |

*Primary Examiner*—Robert A. Hafer
*Assistant Examiner*—Kerry Owens
*Attorney, Agent, or Firm*—Hugh D. Jaeger

[57] ABSTRACT

A method and apparatus for treating patients suffering from glaucoma. A hollow needle is inserted into the eye and advanced across the anterior chamber until the tip punctures the opposite anterior chamber angle wall, exiting the eye under the conjunctiva. The excess pressure is acutely relieved by seepage of the aqueous fluid into the subconjunctival space. A stainless steel helix is ejected from the hollow needle and lodged in the puncture wound of the anterior chamber wall. Sealing the anterior chamber angle puncture wound by normal healing processes is thus prevented and excess pressure is relieved chronically by aqueous fluid seepage through the wound to the subconjunctival space. In a variation of the technique the needle is not passed through the anterior chamber, but the helix is delivered ab externo into the chamber angle.

11 Claims, 7 Drawing Sheets

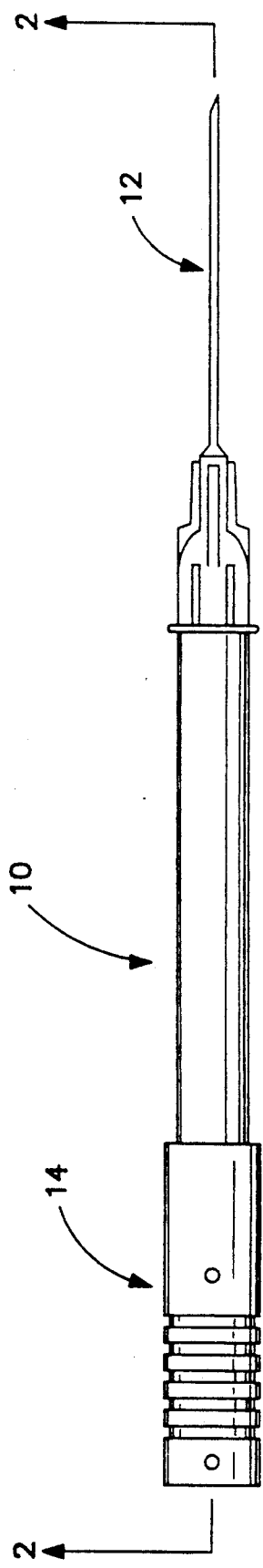
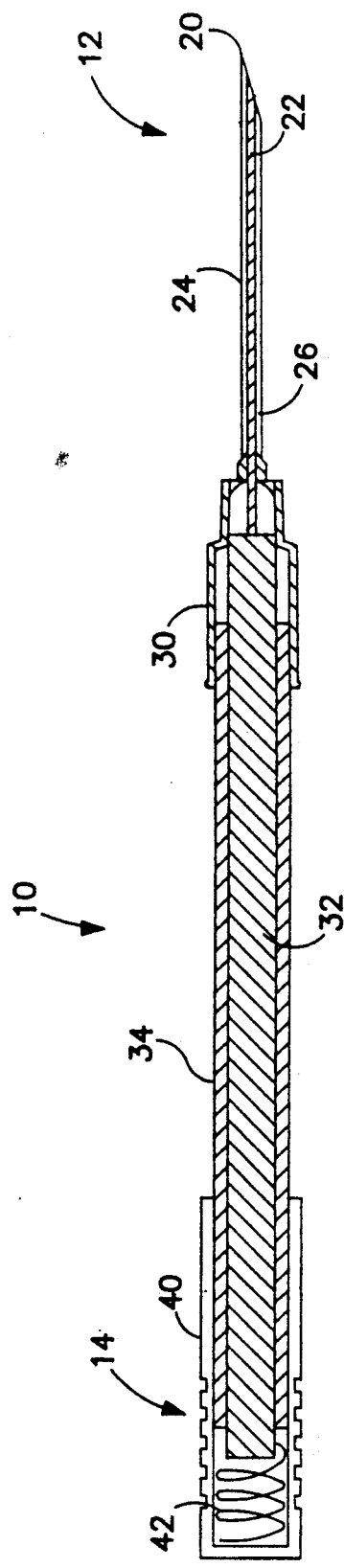
FIG. 1
FIG. 2

GONIO SETON

BACKGROUND OF THE INVENTION

1. Field of the Invention

The present invention pertains to an ophthalmic surgical device, and more importantly, pertains to a specific adaptation of the gonio puncture surgical technique, utilizing a hollow needle rather than a knife.

2. Description of the Prior Art

Glaucoma is one of the chief causes of blindness in adults in the United States and Europe. It is a condition in which intraocular pressure becomes too high and destroys ganglion cells of the retina and the nerve fibers of the optic nerve producing blindness. When the intraocular pressure cannot be controlled with medications, surgery is necessary.

In the normal eye, fluid is pumped in by the epithelial cells lining the surface of the ciliary body. This fluid passes forward through the pupil and into the anterior chamber of the eye. It is drained through a sieve-like filter called the trabecular meshwork, into the drainage Channel of Schlemm and out into the aqueous veins. In patients with glaucoma this drainage mechanism fails causing build up of excess pressure. The purpose of surgery is to create a new drainage system to maintain a lower ambient pressure.

The commonly employed operation today is a fistulizing procedure called trabeculectomy. In this operation the conjunctiva is lifted away from the sclera, and a flap of sclera is lifted extending far enough forward to expose the normal filtering area (the limbus), an opening is made through this limbal area into the anterior chamber, removing a section of tissue to create a permanent defect, and the scleral flap is replaced (as a guard) and the conjunctiva closed.

The operation has technical problems, and a number of well recognized hazards. In addition, it fails immediately in at least 15% of patients, and long term in a much higher percentage. Because a large area of the limbus has been disturbed (about 25%) and because of the damage to the eye that may be produced by the postoperative inflammation that such extensive surgery causes and other possible complications, re-operation is difficult and the number of re-operations possible is limited.

A much simpler procedure has been practiced from time to time, going back as far at least as Von Graefe in the 1850s, used extensively by Barkan in the 1930s and 40s, and still employed in some third world countries where speed, simplicity, and lack of complications outweigh the high failure rate. This procedure is called gonio puncture. In this operation a thin knife is simply introduced across the anterior chamber and a puncture made from inside the eye outward into the space beneath the conjunctiva. The knife is then withdrawn and fluid allowed to drain through this puncture wound. There are no flaps, no sutures, very few complications, and almost no postoperative reaction. Unfortunately, there is a high failure rate, simply because the puncture wound heals.

There is a long history of the use of setons to try to improve the success rate of ordinary filtering surgery. Materials have included the patient's own iris and a variety of metals and plastics. The latter have been fashioned to act as wicks, stints, or tubes. The procedure for placing these devices is a modification of a standard filtering operation. Unfortunately, the same postoperative inflammatory and healing response which causes filtering surgery to fail also seals off the seton, so that most of these devices have had a high rate of failure and very little popularity. There are a few current seton approaches which have a higher rate of success, but these involve very extensive surgery, very large devices, and are used only in desperate cases.

The present invention combines the simplicity and safety of gonio puncture with the advantages of a seton to keep the puncture wound open. It can be repeated, if needed, much more readily because of the minimal disturbance of the eye produced by this approach.

SUMMARY OF THE INVENTION

The present invention employs a gonio seton needle which enters the limbus and is advanced until it punctures the opposite anterior chamber angle. This needle is equipped with a plunger inside, which will deliver a tiny open stainless steel spiral. When the plunger on the back of the needle is pressed, it delivers the tiny spiral of stainless steel into the track created by the needle. Because of the openness of the spiral, it keeps a path open for aqueous flow through the puncture wound and under the conjunctiva, thus lowering intraocular pressure. A stainless steel spiral is employed rather than a fine tube, because experience shows that the aperture of a tube is more easily blocked by iris tissue, inflammatory debris, fibrin, etc.

The technique of surgery consists of entering the anterior chamber with the gonio seton needle through the libus at the temporal side and puncturing the chamber angle at the opposite side until the subconjunctival space has been reached. The drainage of a small amount of fluid will cause an elevation of the conjunctiva over the second puncture site. As the needle is withdrawn, the plunger of the needle is pressed forward depositing the stainless steel spiral in the wound that has been made on the opposite side of the anterior chamber, so that this wound will be held open. The needle is now withdrawn completely from the eye leaving the gonio seton in place.

The operation takes very little time and produces minimum trauma to ocular tissues. No dissection is necessary and no sutures are used. There is, therefore, minimum postoperative inflammation and minimum damage to ocular tissues. These factors increase the chances of success. On the other hand, should the operation fail, it can be repeated, again with the minimum surgery and minimum trauma to the eye. Even in the case of failure, one has not done much harm, in marked distinction to trabeculectomy and other filtering operations.

There is provided a gonio seton instrument having a central tubular body flanked on one end by a tubular concentric actuator member, which is secured by a safety lock, and on the opposing end a hallow gonio puncture needle which includes a gonio seton in the form of a stainless steel open spiral in the central gonio puncture needle space.

One significant aspect and feature of the present invention is a technique for treating glaucoma which produces a minimum of trauma. This occurs because the only wound created in the eye is a small puncture wound, and the purpose of the gonio seton is to ensure that this small puncture wound does not heal with time.

Another significant aspect and feature of the present invention is an apparatus for the placement of a seton which chronically maintains a path for relieving excess pressure in the anterior chamber.

A further significant aspect and feature of the present invention is an apparatus for the treatment of glaucoma which is easily explantable. Because of the minimal trauma at implant and the ease of explant, the procedure is nearly completely reversible and may be repeated if needed.

BRIEF DESCRIPTION OF THE DRAWINGS

Other objects of the present invention and many of the attendant advantages of the present invention will be readily appreciated as the same becomes better understood by reference to the following detailed description when considered in connection with the accompanying drawings, in which like reference numerals designate like parts throughout the figures thereof and wherein:

FIG. 1 is a plan view of a gonio puncture device;

FIG. 2 is a sectioned view of a gonio puncture device;

DETAILED DESCRIPTION OF THE PREFERRED EMBODIMENTS

Figure 3:
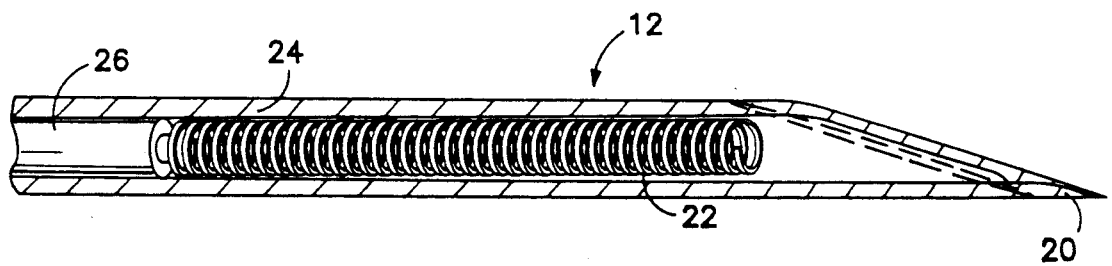
FIG. 3 is a sectioned view of the distal tip of a gonio puncture needle with the gonio seton in the preprocedure position.

FIG. 1 is a plan view of a gonio puncture device. At the distal end 12 is a hollow needle of approximately 24 gauge. The distal tip of distal end 12 is diagonal and sharpened as is further explained below. This section is preferable made of stainless steel. The main body 10 of the gonio puncture device has a handle for ease of grasping by the physician. It is preferably made of plastic. The proximal end of the gonio puncture device has a plunger assembly 14, which is longitudinally slideable with regard to main body 10. This relationship is explained in detail below.

FIG. 2 is a sectioned view of the gonio puncture needle. The plunger assembly 14 has a movable external plunger 40 which is slideably mounted concentric to rigid tube 34 of main body 10. Within rigid tube 34 is main body advancement rod 32 which may be solid or contain a central lumen as shown. Movable external plunger 40 is coupled to main body advancement rod 32 such that a physician may distally advance main body advancement rod 32 by exerting a slight force with the thumb on movable external plunger 40. Small return spring 42 is coupled at its distal end to rigid tube 34 and at its proximal end to movable external plunger 40. Small return spring 42 is properly tensioned to maintain movable external plunger 40 and hence main body advancement rod 32 sufficiently proximal to permit the gonio seton to be totally enclosed within distal end 12 as explained in more detail below.

A slide-on needle holder 30 is fixedly attached to the distal end of rigid tube 34. The proximal end of hollow needle 24 is engaged in slide-on needle holder 30. Hollow needle 24 is a stainless steel surgical needle of about 24 gauge. It has a central lumen and a diagonally shaped tip 20 which has been sharpened in the normal manner for procedures of this type. Gonio seton 22 is located completely within the central lumen of hollow needle 24, but at its very distal tip. Proximal to gonio seton 22 and within the central lumen of hollow needle 24 is ejector 26. This is a rod which is mechanically responsive to main body advancement rod 32 such that distal movement of main body advancement rod 32 causes ejector 26 to move distally and push gonio seton 22 from the distal end of hollow needle 24.

FIG. 3 is a sectioned view of distal tip 12 of the gonio puncture needle wherein all referenced components are as previously described. It can be readily seen that ejector 26 abuts gonio seton 22 within the central lumen of hollow needle 24. It can also be readily seen that distal end 12 is diagonal in shape and sharpened as is known in the art.

Figure 4:
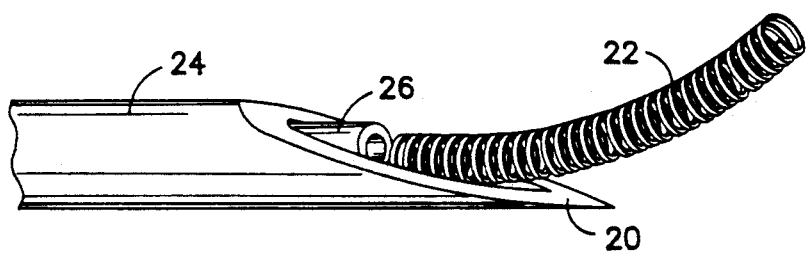
FIG. 4 is a view of the distal tip of a gonio puncture needle with the gonio seton partially ejected.

FIG. 4 is a view of gonio seton 22 as it is ejected from the central lumen of hollow needle 24 by distal movement of ejector 26.

Figure 5:
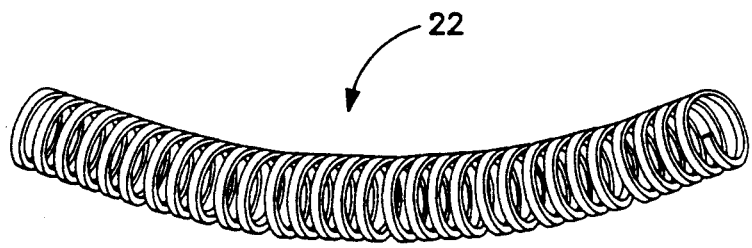
FIG. 5 is a plan view of the gonio seton.

FIG. 5 is a plan view of gonio seton 22. Because it is chronically implanted, it must be made of a biocompatible material suitable for long term implant. Preferably gonio seton 22 is made of 50 micron, hardened stainless steel, although other materials will work equally well. Gonio seton 22 is a helix which is wound in multifilar form. The embodiment shown, by way of example and not to be considered as limiting of the invention, is a multifilament coil.

Figure 6:
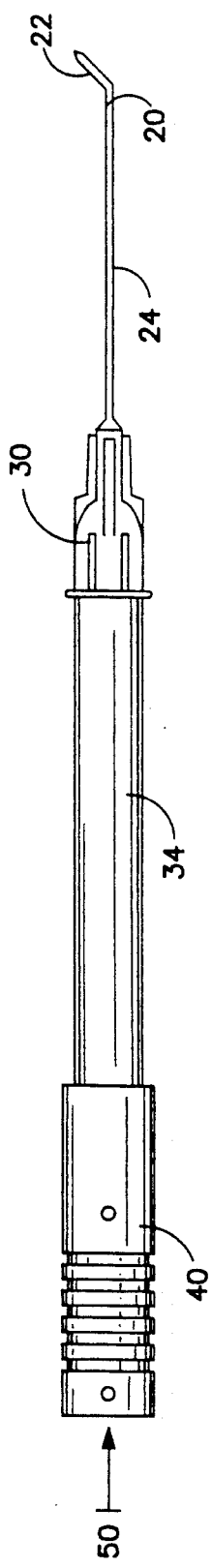
FIG. 6 is a plan view of a gonio puncture device with the gonio seton partially ejected.

FIG. 6 is a plan view of the puncture needle with gonio seton partially ejected, wherein all components are as previously described. Gonio seton 22 is ejected by application of force 50 by the physicians thumb.

Figure 7:
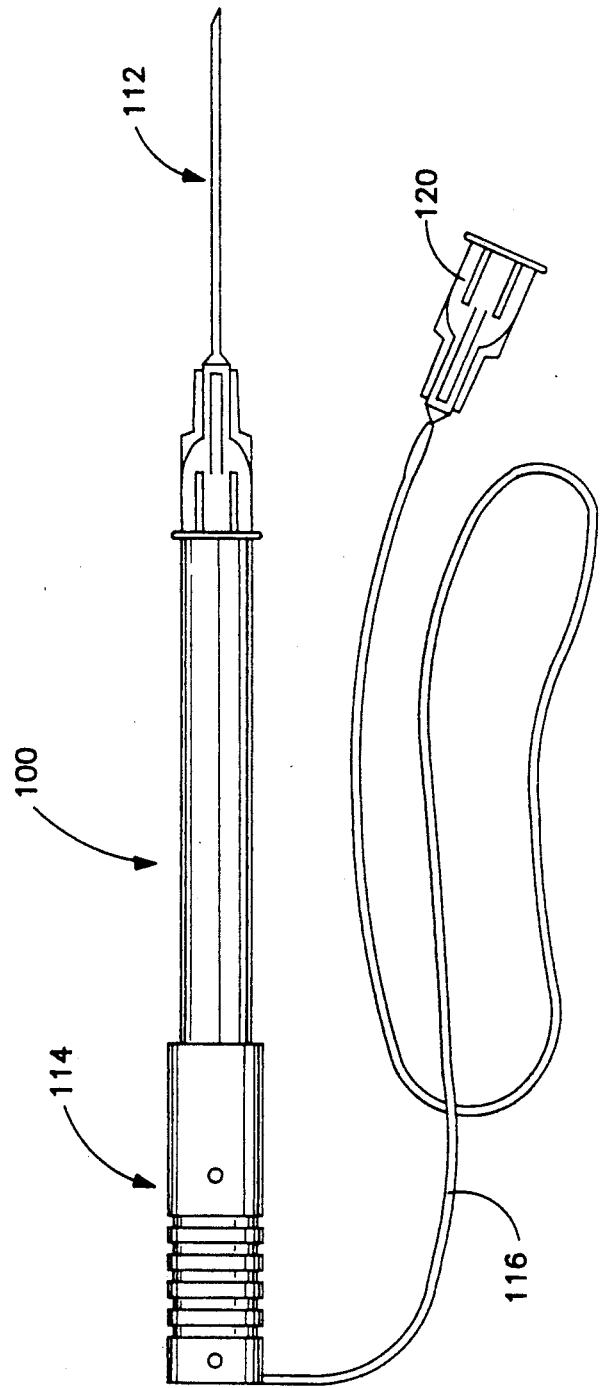
FIG. 7 is a plan view of an alternate embodiment of a gonio puncture device with an apparatus for supplying irrigating solution.

FIG. 7 is a plan view of an alternate embodiment of the gonio puncture needle providing for an apparatus to keep the anterior chamber deepened with irrigating fluid during the procedure. Distal end 112, main body 100, and plunger assembly 114 correspond to distal end 12, main body 10 and plunger assembly 14 as previously described, except that sufficient space must be provided in the internal structure to permit application of the irrigation fluid. Alternatively, a separate lumen may be provided.

Irrigation is accomplished by forcing an irrigating solution such as balanced salt solution into receptor 120 using a syringe. The fluid proceeds through flexible tubing 116 to the proximal end of the alternative embodiment of the gonio puncture needle. The fluid is then communicated through plunger assembly 114, main body 100, and distal end 112. The fluid exits distal end 112 through the hollow tip and is thus applied to the tissue to be irrigated.

MODE OF OPERATION

Figure 8:
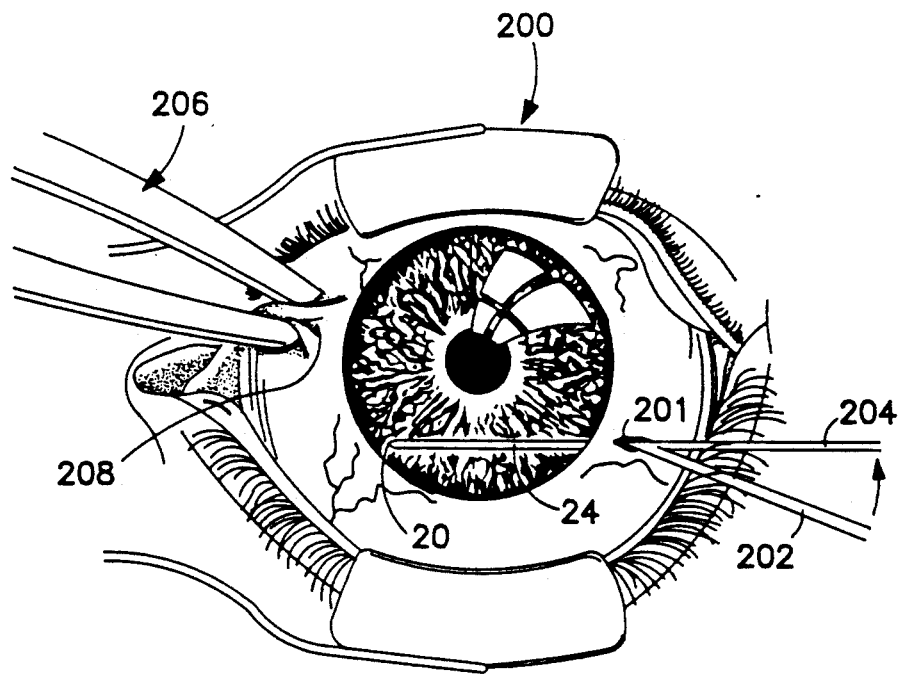
FIG. 8 is a view of the patient's eye showing proper insertion of the gonio puncture needle into the opposite anterior chamber angle wall.

FIG. 8 is a view of the eye 200 of a patient which is undergoing the procedure for implantation of the gonio seton. The patient is prepared in the normal manner. Fixation by forceps 206 is applied in the lower nasal quadrant at point 208, including muscle insertion at the fixation point. A temporal limbal perforation is made at point 201 along path 202 which is perpendicular to the scleral surface. After the initial puncture, the needle is turned to a tangential position along path 204. The needle is advanced along path 204 as prepared by diagonal shaped tip 20.

Figure 9:
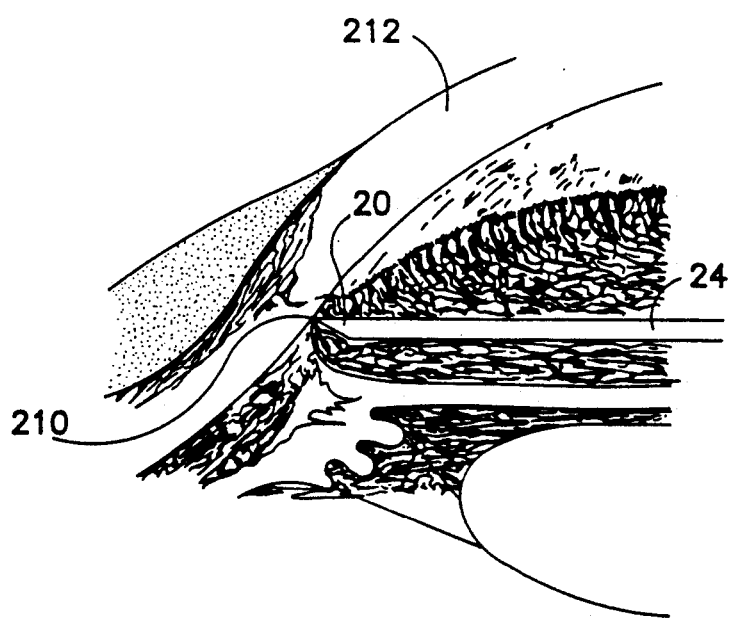
FIG. 9 is a close-up view of the gonio puncture needle exiting the anterior chamber at the process of puncturing the opposite anterior chamber angle wall.

FIG. 9 is a close-up cross sectional view of the patient's eye showing hollow needle 24 advanced to the point that diagonally shaped tip 20 is lodged against point 210 of the wall of the anterior chamber angle 212. The capsule wall is punctured at this point.

Figure 10:
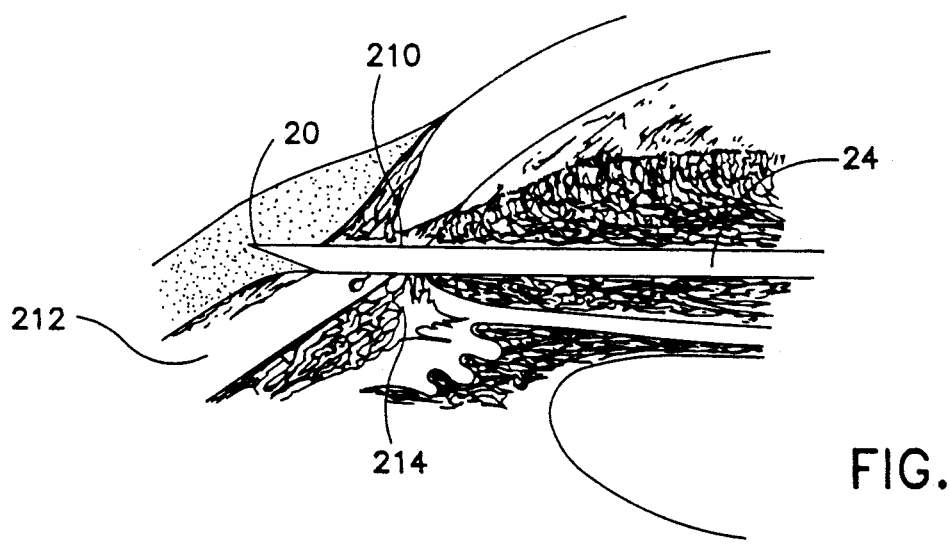
FIG. 10 is a close-up view showing the needle tip exiting through the chamber angle wall into the subconjunctival space.

FIG. 10 shows hollow needle 24 advanced to the farthest point in the procedure creating a subconjunctival bleb. Anterior chamber angle wall in the limbal area 212 has been punctured at point 210, and aqueous fluid is permitted to seep into subconjunctival space 214 to acutely relieve excess pressure. Whenever needed, the physician may deepen the anterior chamber using a balanced salt solution when using the alternative embodiment of FIG. 7.

Figure 11:
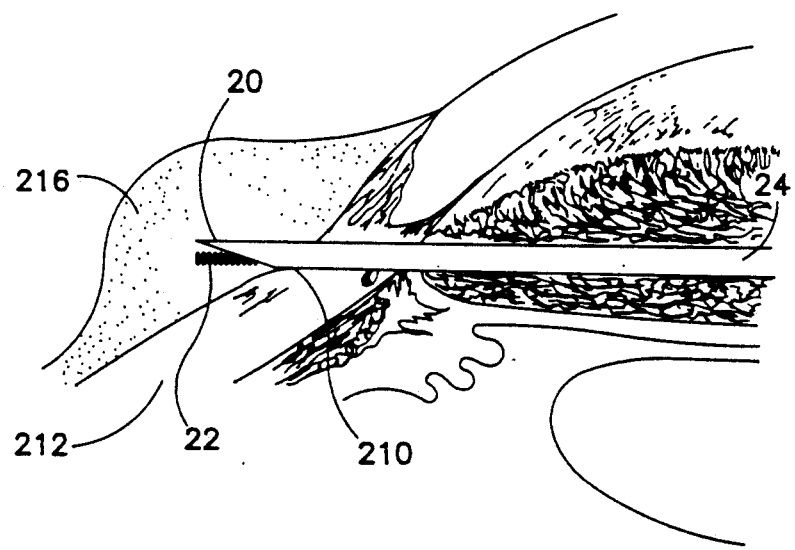
FIG. 11 is a close-up view of the beginning of extrusion of the gonio seton helix into the puncture wound.

FIG. 11 shows the ejection of gonio seton 22.

Figure 12:
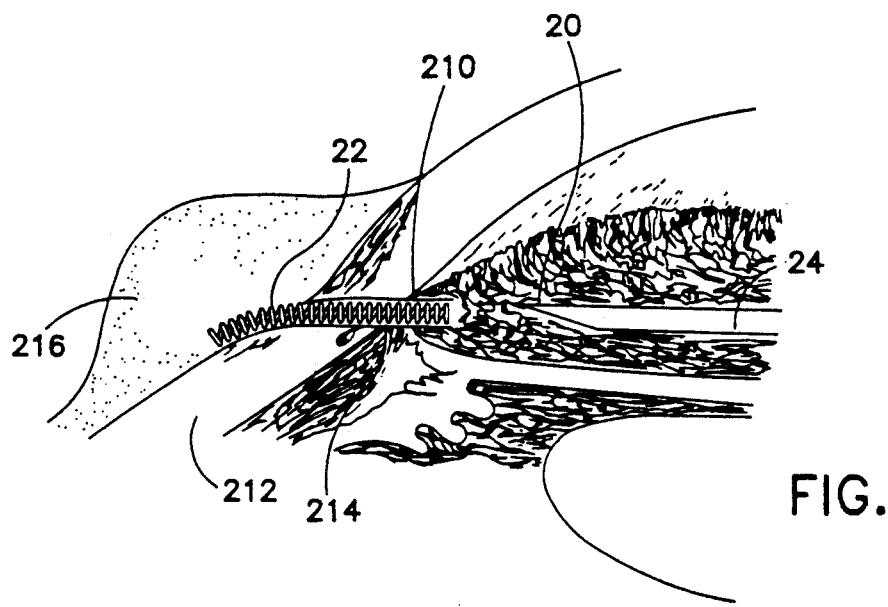
FIG. 12 is a close-up view of the gonio seton as completely implanted.

FIG. 12 shows gonio seton 22 as permanently implanted. It is positioned in the Lagrange fistulating zone. Hollow needle 24 is retracted as shown.

Figure 13A:
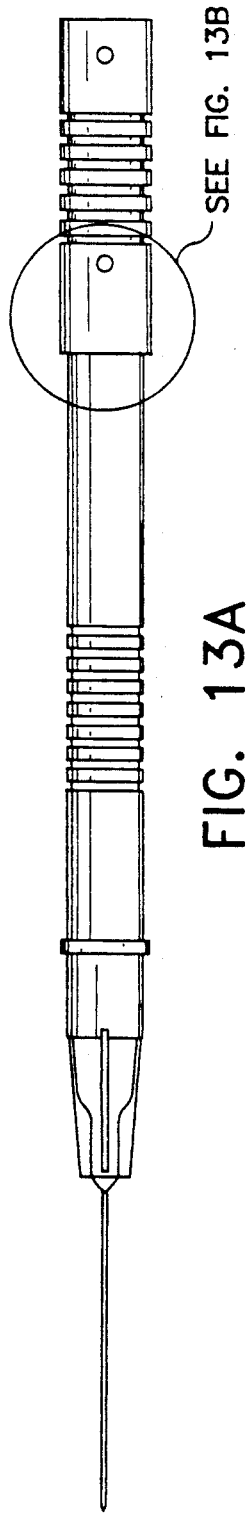
FIG. 13 is a close-up view of the safety lock.
Figure 13B:
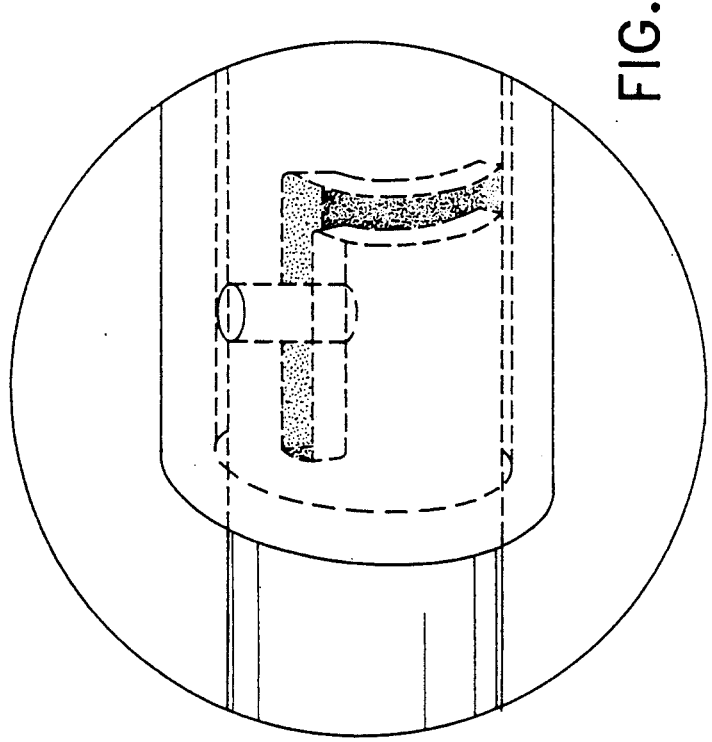

FIG. 13 shows the safety lock, which secures the plunger assembly 14. Thus, inadvertent sliding in a longitudinal direction is prevented.

Figure 14A:
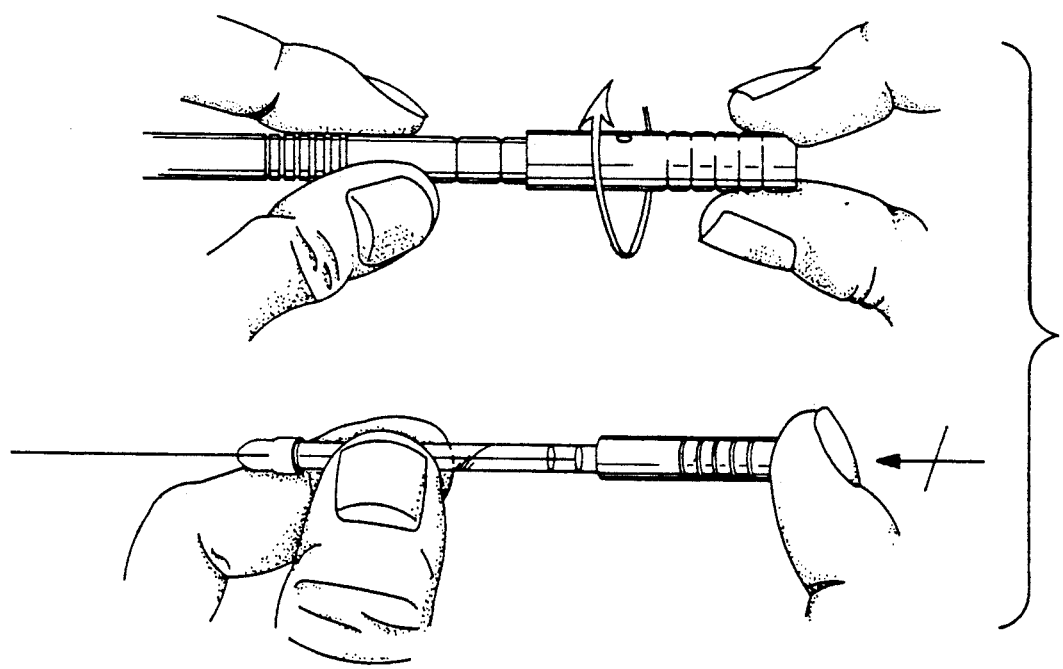
FIG. 14 shows the locking (A) and unlocking (B) mechanism.

FIG. 14A shows the locking mechanism. The plunger assembly is prevented from sliding when the lock has been secured by a clockwise rotation.

Figure 14B:
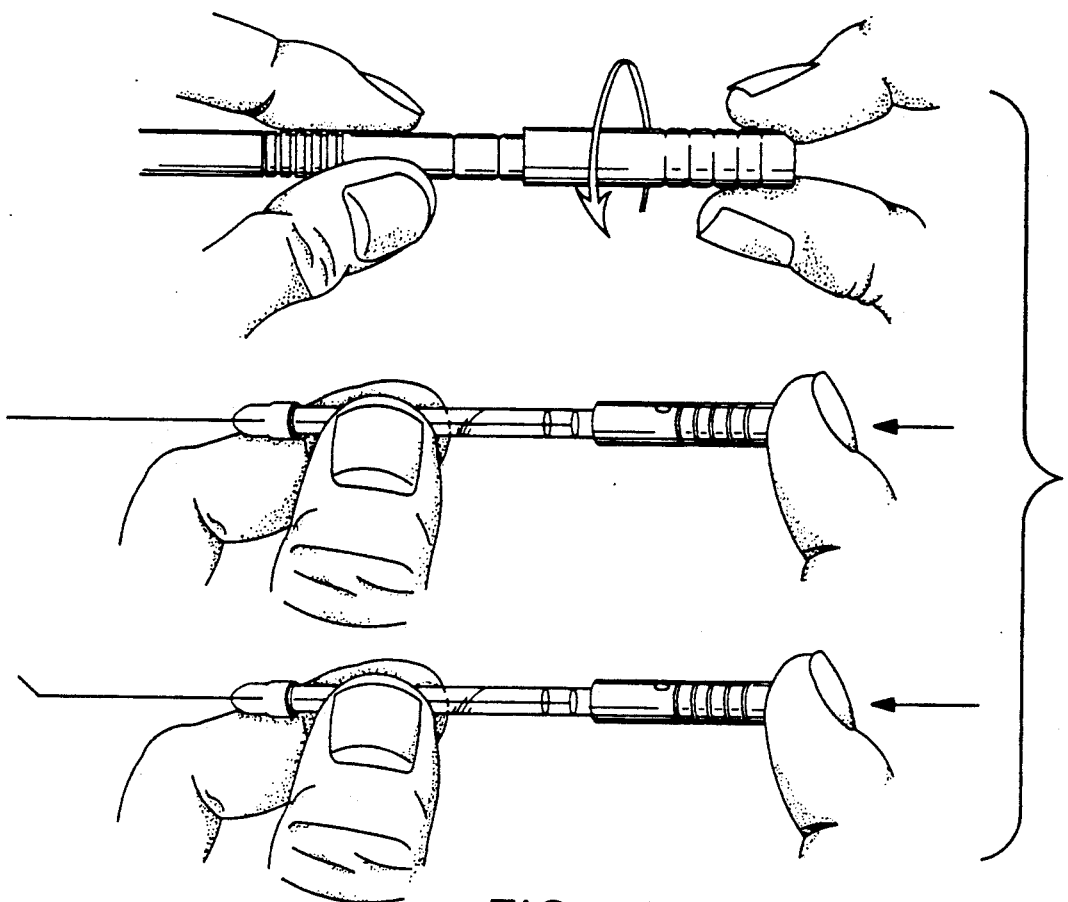

FIG. 14B shows the unlocking of the safety lock by an anticlockwise rotation. After this, the plunger assembly can be made to slide in a longitudinal direction by compression on its rear part, which will cause an extrusion of the gonio seton. The two marker lines in front of the plunger assembly indicate the position of the plunger.

Having thus described the preferred embodiments of the present invention, those of skill in the art will be readily able to apply these teachings to other embodiments without deviating from the scope of the claims hereto attached.

I claim:

1. A method of treating glaucoma comprising:
   a. inserting a needle containing a spiral gonio seton into the limbal area of an eye containing said glaucoma, said spiral gonia seton including spaces between adjacent helices;
   b. advancing said needle laterally to said eye puncturing the anterior chamber angle wall;
   c. permitting aqueous fluid from said anterior chamber to seep into the subconjunctival space creating a subconjunctival bleb;
   d. providing a multiple orificed drainage path through said spaced in said helices of said spiral gonia seton by ejecting said spiral gonio seton from said needle into said subconjunctival bleb; and
   e. retracting said needle.

2. A method according to claim 1 further comprising irrigating said anterior chamber following said permitting step with a balanced salt solution.

3. A method according to claim 2 wherein said irrigating is performed through a lumen within said needle.

4. Apparatus for treating glaucoma comprising:
   a. a needle having a lumen for piercing the anterior chamber angle wall of an eye; and
   b. a helical gonio seton having spaces between adjacent helices for the passage of fluid, said seton being removably located with in said needle.

5. Apparatus according to claim 4 wherein said gonio seton is metallic.

6. Apparatus according to claim 5 wherein said needle has a proximal end and a distal end, and wherein said gonio seton is removable from said distal end.

7. Apparatus according to claim 6 wherein said needle further comprises means for ejecting said gonio seton from said distal end of said needle.

8. Apparatus according to claim 7 wherein said ejecting means is located at said proximal end of said needle.

9. Apparatus according to claim 8 wherein said gonio seton is a helix of stainless steel.

10. Apparatus according to claim 4, wherein said helical gonio seton has a multiple orifice construction.

11. Apparatus according to claim 4, further comprising a handle attached to said needle, said handle comprising a longitudinally slidable plunger assembly for ejecting said gonio seton, said plunger assembly including locking means for preventing the undesirable longitudinal movement of said plunger.

* * * * *